United States Patent
Himmler et al.

(10) Patent No.: US 9,969,717 B2
(45) Date of Patent: May 15, 2018

(54) METHOD FOR PRODUCING SUBSTITUTED ANTHRANILIC ACID DERIVATIVES

(71) Applicant: BAYER INTELLECTUAL PROPERTY GMBH, Monheim (DE)

(72) Inventors: Thomas Himmler, Odenthal (DE); Sergii Pazenok, Solingen (DE); Frank Volz, Cologne (DE); Norbert Lui, Odenthal (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 0 days. days.

(21) Appl. No.: 15/493,087

(22) Filed: Apr. 20, 2017

(65) Prior Publication Data

US 2017/0217934 A1    Aug. 3, 2017

Related U.S. Application Data

(60) Division of application No. 14/924,889, filed on Oct. 28, 2015, which is a continuation of application No. 14/375,496, filed as application No. PCT/EP2013/052350 on Feb. 6, 2013, now abandoned.

(30) Foreign Application Priority Data

Feb. 7, 2012    (EP) .................... 12154290

(51) Int. Cl.
  *C07D 401/00*    (2006.01)
  *C07D 401/14*    (2006.01)

(52) U.S. Cl.
  CPC .................. *C07D 401/14* (2013.01)

(58) Field of Classification Search
  CPC .................................................. C07D 401/01
  USPC ...................................................... 546/275.4
  See application file for complete search history.

(56) References Cited

U.S. PATENT DOCUMENTS

| | | |
|---|---|---|
| 6,632,815 B2 | 10/2003 | Zhu et al. |
| 6,635,657 B1 | 10/2003 | Beight et al. |
| 7,456,169 B2 | 11/2008 | Hasvold et al. |
| 7,491,718 B2 | 2/2009 | Comess et al. |
| 8,101,550 B2 | 1/2012 | Alig et al. |
| 8,871,939 B2 | 10/2014 | Kristjansdottir et al. |
| 9,670,182 B2 * | 6/2017 | Himmler .............. C07D 401/14 |
| 2004/0068012 A1 | 4/2004 | Comess et al. |
| 2011/0306645 A1 | 12/2011 | Fischer et al. |
| 2012/0101133 A1 | 4/2012 | Pazenok et al. |

FOREIGN PATENT DOCUMENTS

| | | |
|---|---|---|
| EP | 0 034 292 A2 | 8/1981 |
| JP | S 56-125346 A | 10/1981 |
| JP | 2004-4374 A | 2/2004 |
| JP | 2004-531475 A | 10/2004 |
| JP | 2005-532367 A | 10/2005 |
| JP | 2009-543861 A | 10/2009 |
| WO | 9728134 A1 | 8/1997 |
| WO | 2003015519 A1 | 2/2003 |
| WO | 03106427 A2 | 12/2003 |
| WO | 2004067528 A1 | 8/2004 |
| WO | 2006062978 A1 | 6/2006 |
| WO | 2008010897 A2 | 1/2008 |
| WO | 2008070158 A1 | 6/2008 |
| WO | 2008082502 A2 | 7/2008 |
| WO | 2009006061 A2 | 1/2009 |
| WO | 2009061991 A1 | 5/2009 |
| WO | 2009085816 A1 | 7/2009 |

(Continued)

OTHER PUBLICATIONS

International Search Report received in PCT/EP2013/052350, dated Mar. 14, 2013.

(Continued)

*Primary Examiner* — Nizal Chandrakumar
(74) *Attorney, Agent, or Firm* — McBee Moore Woodward & Vanik IP, LLC

(57) ABSTRACT

The present invention relates to a process for preparing substituted anthranilic acid derivatives of the formula (I)

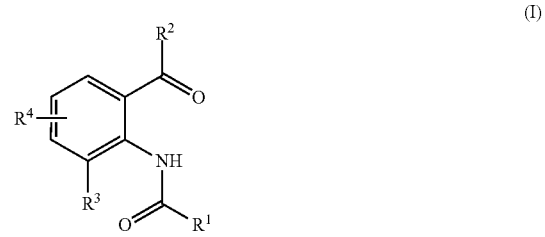

in which $R^1$, $R^2$, $R^3$ and $R^4$ are each as defined in the description, by conversion of compounds of the general formula (IV) in the presence of a palladium catalyst and carbon monoxide. The present invention likewise relates to compounds of the general formula (IV).

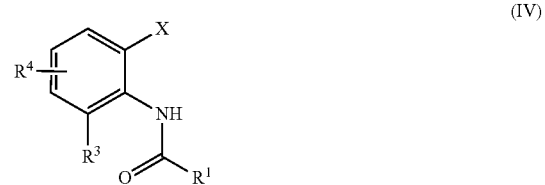

7 Claims, No Drawings

(56) References Cited

FOREIGN PATENT DOCUMENTS

| WO | 2009111553 A1 | | 9/2009 | |
| WO | WO 2010069502 | * | 6/2010 | ........... C07D 401/14 |
| WO | 2011157664 A1 | | 12/2011 | |
| WO | 2012103436 A1 | | 8/2012 | |
| WO | WO 2013117601 | * | 8/2013 | ........... C07D 401/14 |

OTHER PUBLICATIONS

Valentine et al., Practical Catalytic Synthesis of Anthanilic Acids, Journal of Organic Chemisty, BD. 46, Nr. 22, 1981, 4614-4617, XP000197505.

Rama et al., A new convergetn synthesis of WS-5995-B, an anticoccidial antibiotic from Streptomyces auranticoor, Tetrahedron, Bd. 50, Nr. 8, 1994, Seiten 2543-2550, XP055031465, ISS: 0040-420.

Zhili, et al., Design, Synthesis and Insecticidal Evaluation of Novel Pyrazolecarboxamides Containing Cyano Substituted N-Pyridylpyrazole, Chinese Journal of Chemistry, Bd. 28, Nr. 9, 2010, 1757-1760, XP055009637.

McNulty, et al., Efficient palladium-catalysed carbonylative and Suzuki-Miyaura cross-coupling reactions with bis(di-ter-butylphosphino)-o-xylene, Tetrahedron Letters, Bd. 50, Nr. 20, 2009, 2342-2346, XP026063193.

Lahm, Insecticidal anthranilic diamides: A new class of potent ryanodine receptor activators, Bioorganic & Med. Chem. Letters 15 (2005) 4898-4906.

Clark, Synthesis of insecticidal fluorinated anthranilic diamides, Bioorganic & Med. Chem. Letters 16 (2008) 3163-3170.

Sorgi et al., Encyclopedia of Reagents for Organic Synthesis, 2001, doi:10.1002/047084289X.rt164.

Fulford, e-EROS, Encyclopedia of Reagents for Organic Synthesis (2001), John Wiley & Sons, Chichester, UK) Coden:69KUHI.

Seo et al., J. Org. Chem. 2006, vol. 71, pp. 8891-8900.

Valentine et al., Journal of Organic Chemistry, 1981, vol. 46, pp. 4614-4617.

Montalbetti et al. Tetrahedron, 2005 61. 10827-10852.

* cited by examiner

METHOD FOR PRODUCING SUBSTITUTED ANTHRANILIC ACID DERIVATIVES

CROSS REFERENCE TO RELATED APPLICATIONS

This application is a divisional application of U.S. application Ser. No. 14/924,889, filed Oct. 28, 2015, which is a continuation application of U.S. application Ser. No. 14/375,496, filed Jul. 30, 2014, which is a § 371 National Stage Application of PCT/EP2013/052350, filed Feb. 6, 2013, which claims priority to European Application No. 12154290.6, filed Feb. 7, 2012, the contents all of which are incorporated herein by reference in their entireties.

BACKGROUND

Field of the Invention

The present invention relates to a novel process for preparing substituted anthranilic acid derivatives of the formula (I)

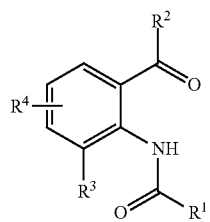

(I)

in which
  $R^1$ is optionally singly or multiply, identically or differently fluorine- or chlorine-substituted $C_1$-$C_6$-alkyl, or $C_6$-$C_{10}$-aryl, or is a hetaryl radical of the general formula (II)

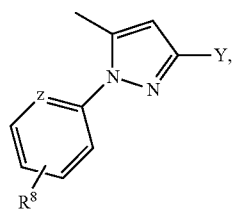

(II)

$R^1$ is preferably $C_1$-$C_3$-alkyl, $C_6$-aryl or a hetaryl radical of the general formula (II),
  $R^1$ is more preferably $C_1$-$C_2$-alkyl or a hetaryl radical of the general formula (II),
where
  $R^8$ is $C_1$-$C_6$-alkyl, $C_3$-$C_6$-cycloalkyl, $C_1$-$C_4$-alkoxy, $C_1$-$C_4$-alkylthio, $C_1$-$C_4$-alkylsulphinyl, $C_1$-$C_4$-alkylsulphonyl, which may optionally be mono- or polysubstituted identically or differently by fluorine or chlorine, or is fluorine, chlorine, cyano, alkylamino, dialkylamino, cycloalkylamino or $C_3$-$C_6$-trialkylsilyl,
  $R^8$ is preferably fluorine, chlorine or $C_1$-$C_6$-alkyl,
  $R^8$ is more preferably fluorine or chlorine,
  Z is CH or N,
  Z is preferably and more preferably N,
and
  Y is hydrogen, fluorine, chlorine, optionally singly or multiply, identically or differently fluorine- or chlorine-substituted $C_1$-$C_6$-alkyl, $C_3$-$C_6$-cycloalkyl, $C_1$-$C_4$-alkoxy, $C_1$-$C_4$-alkylthio, $C_1$-$C_4$-alkylsulphinyl, $C_1$-$C_4$-alkylsulphonyl, or is cyano, alkylamino, dialkylamino, cycloalkylamino, $C_3$-$C_6$-trialkylsilyl or a radical of the general formula (III)

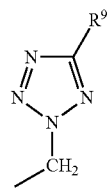

(III)

where
  $R^9$ is $C_1$-$C_5$-alkyl which may optionally be mono- or polysubstituted identically or differently by halogen,
  $R^9$ is preferably $C_1$-$C_3$ perfluoroalkyl,
  $R^9$ is more preferably $CF_3$ or $C_2F_5$,
  $R^2$ is an $OR^5$ or $NR^6R^7$ radical,
  $R^2$ is preferably and more preferably $OR^5$,
  $R^2$ is likewise preferably and more preferably $NR^6R^7$,
where
  $R^5$, $R^6$ and $R^7$ are each independently hydrogen, $C_1$-$C_6$-alkyl, or $C_6$-$C_{10}$-aryl,
  $R^5$, $R^6$ and $R^7$ are preferably each independently hydrogen, $C_1$-$C_3$-alkyl or $C_6$-aryl,
  $R^5$, $R^6$ and $R^7$ are more preferably each independently hydrogen or $C_1$-$C_2$-alkyl,
  $R^3$ is hydrogen, optionally singly or multiply, identically or differently fluorine- or chlorine-substituted $C_1$-$C_6$-alkyl, $C_1$-$C_6$-alkoxy or $C_3$-$C_6$-cycloalkyl,
  $R^3$ is likewise halogen,
  $R^3$ is preferably $C_1$-$C_5$-alkyl,
  $R^3$ is more preferably methyl, ethyl or tert-butyl,
  $R^3$ is likewise preferably and more preferably chlorine,
  $R^4$ is hydrogen, fluorine, chlorine, cyano, optionally singly or multiply, identically or differently fluorine- or chlorine-substituted $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-alkylamino, di($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, $SF_5$ or $C_3$-$C_6$-trialkylsilyl,
  $R^4$ is preferably hydrogen, chlorine or cyano,
  $R^4$ is more preferably chlorine or cyano,
characterized in that substituted anthranilic acid derivatives of the formula (IV)

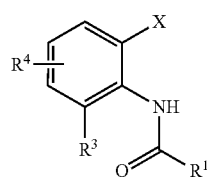

(IV)

in which the $R^1$, $R^3$ and $R^4$ radicals are each as defined above
and
  X is chlorine, bromine or iodine, preferably bromine or iodine, more preferably bromine, are reacted in the presence of a palladium catalyst and optionally of a phosphine ligand simultaneously with carbon monoxide and a compound of the general formula (V)

 (V)

in which $R^5$ is as defined above or a compound of the general formula (VI)

 (VI)

in which $R^6$ and $R^7$ are each as defined above.

Description of Related Art

The literature already states that it is possible to obtain substituted anthranilic acid derivatives of the formula (I) by reaction of anthranilic acid derivatives of the general formula (VII)

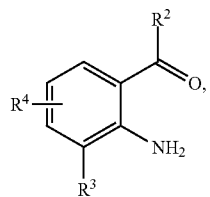 (VII)

with carboxylic acids of the general formula (VIII)

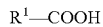 (VIII)

in the presence of agents which activate the carboxyl group for the desired reaction, for example thionyl chloride, oxalyl chloride, phosgene, methanesulphonyl chloride or toluenesulphonyl chloride (WO 2003/015519; WO 2003/106427; WO 2004/067528; WO 2006/062978; WO 2008/010897; WO 2008/070158; WO 2008/082502; WO 2009/006061; WO 2009/061991; WO 2009/085816; WO 2009 111553; Bioorg. & Med. Chem. Lett. 15 (2005) 4898-4906; Bioorg. & Med. Chem. 16 (2008) 3163-3170).

The known reactions can be illustrated by the following reaction schemes, where $R^1$, $R^3$, $R^4$, $R^6$ and $R^7$ have, for example, the definitions given above:

a) $R^2=OR^5$ where $R^5$ is not H, or $NR^6R^7$

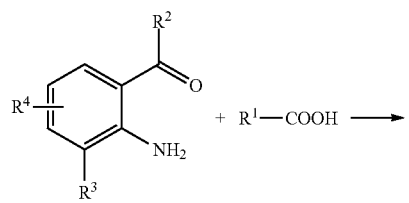

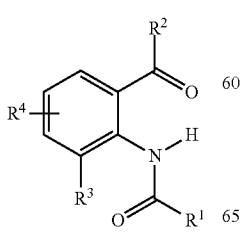

b) $R^2=OR^5$ where $R^5=H$

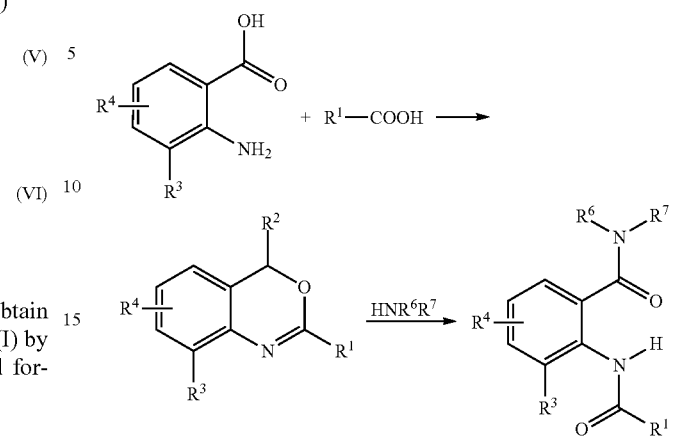

These known methods for preparation of substituted anthranilic acid derivatives of the formula (I) require the availability of the corresponding substituted anthranilic acid derivatives of the general formula (VII). These substituted anthranilic acid derivatives of the general formula (VII) are either known or can be prepared by known organic chemistry methods. Some of these substituted anthranilic acid derivatives of the general formula (VII), however, can be prepared only in a complex manner, in multiple stages and at high cost, which can lead to uneconomically high costs for the end products as a result of unavoidable yield losses.

Substituted anthranilic acid derivatives of the formula (I) are of high interest as compounds having known insecticidal efficacy (see, for example, Bioorg. & Med. Chem. Lett. 15 (2005) 4898-4906; Biorg. & Med. Chem. 16 (2008) 3163-3170). Further, it is already known, that substituted anthranilic acid derivatives of the general formula (VII) can be obtained by reacting substituted anthranilic acid derivatives of the general formula (IX) with carbon monoxide in the presence of a palladium catalyst, of a ligand, of a primary amine and a base (WO 2012/103436). However, it is not known whether anthranilic acid amides of the general formula (IV) can be used correspondingly.

SUMMARY

It is therefore an object of the present invention to provide a novel, more economically viable process for preparing substituted anthranilic acid derivatives of the formula (I).

The object was achieved according to the present invention by a process for preparing anthranilic acid derivatives of the general formula (I), characterized in that substituted anthranilic acid derivatives of the general formula (IX)

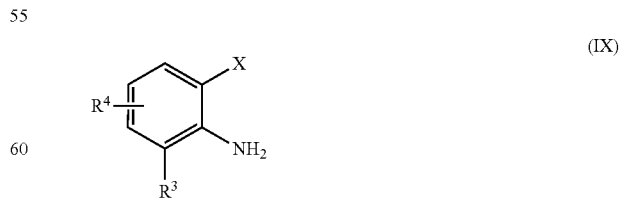 (IX)

in which X, $R^3$ and $R^4$ are each as defined above are reacted with acids of the general formula (VIII) to give the substituted anthranilic acid derivatives of the formula (IV)

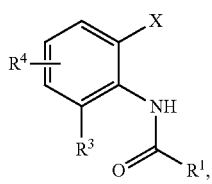

and the latter are then reacted in the presence of a palladium catalyst and optionally of a phosphine ligand simultaneously with carbon monoxide and a compound of the general formula (V)

in which $R^5$ is as defined above or a compound of the general formula (VI)

in which $R^6$ and $R^7$ are each as defined above to give the substituted anthranilic acid derivatives of the general formula (I).

DETAILED DESCRIPTION OF A PREFERRED EMBODIMENT

The process according to the invention can be illustrated by the following scheme:

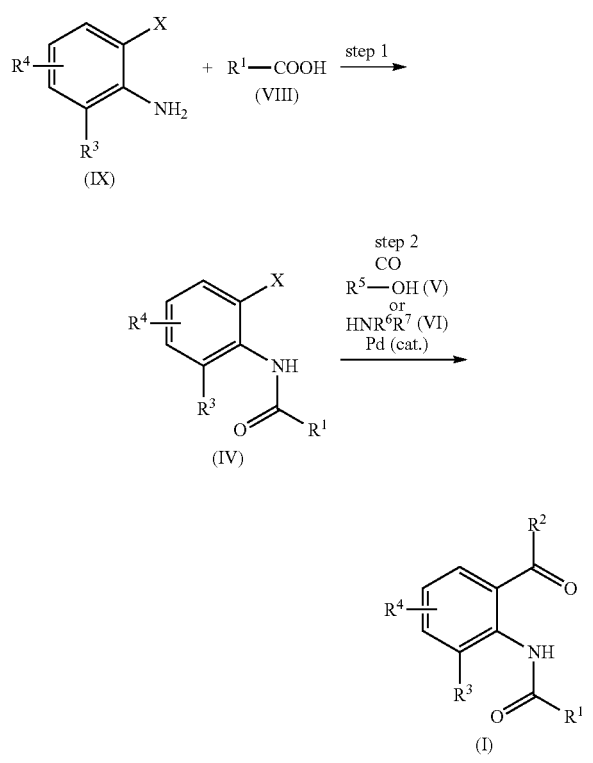

The present invention likewise provides novel compounds of the general formula (IV)

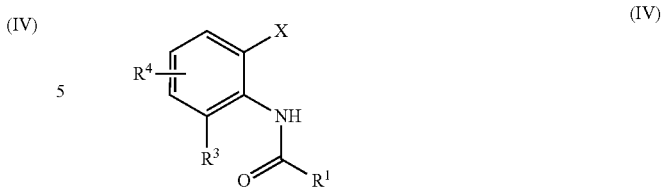

in which the $R^1$, $R^3$, $R^4$ and X radicals are each as defined above.

Preference is given to compounds of the general formula (IV) in which
  $R^1$ is optionally singly or multiply, identically or differently fluorine- or chlorine-substituted $C_1$-$C_6$-alkyl, or $C_6$-$C_{10}$-aryl, or is a hetaryl radical of the general formula (II)

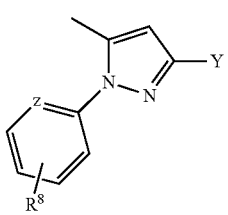

where
  $R^8$ is optionally singly or multiply, identically or differently fluorine- or chlorine-substituted $C_1$-$C_6$-alkyl, $C_3$-$C_6$-cycloalkyl, $C_1$-$C_4$-alkoxy, $C_1$-$C_4$-alkylthio, $C_1$-$C_4$-alkylsulphinyl, $C_1$-$C_4$-alkylsulphonyl, or is fluorine, chlorine, cyano, alkylamino, dialkylamino, cycloalkylamino or $C_3$-$C_6$-trialkylsilyl, preferably fluorine, chlorine or $C_1$-$C_6$-alkyl, more preferably fluorine or chlorine,
  Z is CH or N, preferably N,
and
  Y is hydrogen, fluorine, chlorine, optionally singly or multiply, identically or differently fluorine- or chlorine-substituted $C_1$-$C_6$-alkyl, $C_3$-$C_6$-cycloalkyl, $C_1$-$C_4$-alkoxy, $C_1$-$C_4$-alkylthio, $C_1$-$C_4$-alkylsulphinyl, $C_1$-$C_4$-alkylsulphonyl, or is cyano, alkylamino, dialkylamino, cycloalkylamino, $C_3$-$C_6$-trialkylsilyl or a radical of the general formula (III)

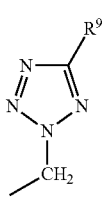

in which
  $R^9$ is $C_1$-$C_5$-alkyl which may be mono- or polysubstituted identically or differently by halogen,
  $R^9$ is preferably $C_1$-$C_3$-perfluoroalkyl,
  $R^9$ is more preferably $CF_3$ or $C_2F_5$,
  $R^3$ is chlorine,
  $R^3$ is likewise methyl,
  $R^4$ is chlorine or cyano,
and
  X is bromine or iodine.

Particular preference is given to compounds of the general formula (IV) in which R¹ is a hetaryl radical of the general formula (II)

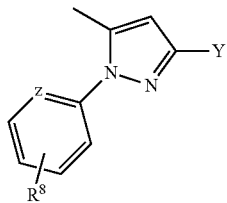

where
R⁸ is fluorine or chlorine,
Z is N,
and
Y is hydrogen, fluorine, chlorine or a radical of the general formula (III)

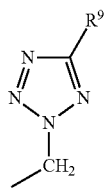

where
R⁹ is $CF_3$ or $C_2F_5$,
R³ is methyl,
R⁴ is chlorine or cyano,
and
X is bromine.

Examples of the particularly preferred compounds of the general formula (IV) include:

N-(2-bromo-4-cyano-6-methylphenyl)-1-(3-chloropyridin-2-yl)-3-{[5-(trifluoromethyl)-2H-tetrazol-2-yl]methyl}-1H-pyrazole-5-carboxamide N-(2-bromo-4-chloro-6-methylphenyl)-1-(3-chloropyridin-2-yl)-3-{[5-(pentafluoroethyl)-2H-tetrazol-2-yl]methyl}-1H-pyrazole-5-carboxamide General definitions: Alkyl groups substituted by one or more fluorine or chlorine atoms (=fluoro- or chloroalkyl groups) are selected, for example, from trifluoromethyl ($CF_3$), difluoromethyl ($CHF_2$), $CCl_3$, $CFCl_2$, $CF_3CH_2$, $C_1CH_2$, $CF_3CCl_2$.

Alkyl groups in the context of the present invention, unless defined differently, are linear or branched hydrocarbyl groups.

The definition alkyl and $C_1$-$C_{12}$-alkyl encompasses, for example, the meanings of methyl, ethyl, n-, isopropyl, n, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

Cycloalkyl groups in the context of the present invention, unless defined differently, are cyclic saturated hydrocarbyl groups.

Aryl radicals in the context of the present invention, unless defined differently, are aromatic hydrocarbyl radicals which may have one, two or more heteroatoms selected from O, N, P and S and may optionally be substituted by further groups.

Arylalkyl groups and arylalkoxy groups in the context of the present invention, unless defined differently, are, respectively, alkyl and alkoxy groups which are substituted by aryl groups and may have an alkylene chain. Specifically, the definition arylalkyl encompasses, for example, the meanings of benzyl and phenylethyl, and the definition arylalkoxy, for example, the meaning of benzyloxy.

Alkylaryl groups (alkaryl groups) and alkylaryloxy groups in the context of the present invention, unless defined differently, are, respectively, aryl groups and aryloxy groups which are substituted by alkyl groups, may have a $C_{1-8}$-alkylene chain and may have, in the aryl skeleton or aryloxy skeleton, one or more heteroatoms selected from O, N, P and S.

Step 1

Anthranilic acid derivatives of the formula (IV) can be prepared as follows:

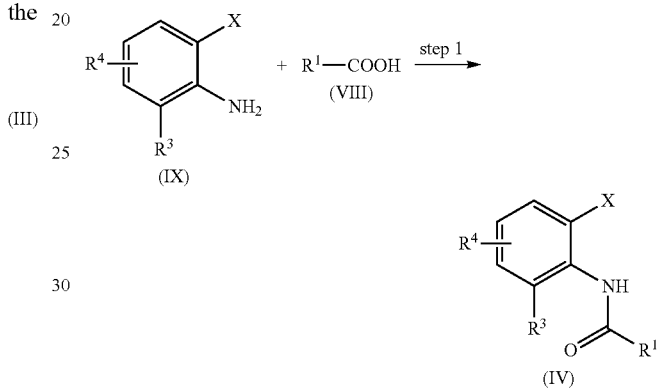

The reaction is performed in the presence of a condensing agent. Suitable agents for this purpose are all agents customary for such coupling reactions. Examples include acid halide formers such as phosgene, phosphorus tribromide, phosphorus trichloride, phosphorus pentachloride, phosphorus oxychloride, oxalyl chloride or thionyl chloride; anhydride formers such as ethyl chloroformate, methyl chloroformate, isopropyl chloroformate, isobutyl chloroformate or methanesulphonyl chloride; carbodiimides such as N,N'-dicyclohexylcarbodiimide (DCC) or other customary condensing agents such as phosphorus pentoxide, polyphosphoric acid, 1,1'-carbonyldiimidazole, 2-ethoxy-N-ethoxycarbonyl-1,2-dihydroquinoline (EEDQ), triphenylphosphine/carbon tetrachloride, bromotripyrrolidinophosphonium hexafluorophosphate, bis(2-oxo-3-oxazolidinyl)phosphine chloride or benzotriazol-1-yloxytris(dimethylamino)phosphonium hexafluorophosphate. It is likewise possible to use polymer-supported reagents, for example polymer-bound cyclohexylcarbodiimide Preference is given to phosgene, mesyl chloride and thionyl chloride.

Process step 1 can optionally be performed in the presence of an inert organic diluent customary for such reactions. These preferably include aliphatic, alicyclic or aromatic hydrocarbons, for example petroleum ether, hexane, heptane, cyclohexane, methylcyclohexane, benzene, toluene, xylene or decalin; halogenated hydrocarbons, for example chlorobenzene, dichlorobenzene, dichloromethane, chloroform, carbon tetrachloride, dichloroethane or trichloroethane; ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones such as acetone, butanone, methyl isobutyl ketone or cyclohexanone; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide, or mixtures thereof.

Process step 1 is generally performed in the presence of a base.

Suitable bases are alkali metal hydroxides, for example lithium hydroxide, sodium hydroxide or potassium hydroxide, alkali metal carbonates, for example $Na_2CO_3$, $K_2CO_3$, and acetates, for example NaOAc, KOAc, LiOAc, and also alkoxides, for example NaOMe, NaOEt, NaOt-Bu, KOt-Bu. Likewise suitable bases are organic bases such as trialkylamines, alkylpyridines, phosphazenes and 1,8-diazabicyclo [5.4.0]undecene (DBU). Preference is given to organic bases such as pyridines, alkylpyridines, for example 2,6-dimethylpyridine, 2-methyl-5-ethylpyridine or 2,3-dimethylpyridine.

Process step 1 of the invention is performed preferably within a temperature range from 20° C. to +100° C., more preferably at temperatures of 30° C. to +80 ° C., more preferably at 30-60° C.

Process step 1 of the invention is generally performed under standard pressure. Alternatively, however, it is also possible to work under vacuum or under elevated pressure in an autoclave.

The reaction time may, according to the batch size and the temperature, be selected within a range between 1 hour and several hours.

Process step 1 can optionally be performed in the presence of a catalyst. Examples include 4-dimethylaminopyridine or 1-hydroxybenzotriazole.

Step 2

Substituted anthranilic acid derivatives of the general formula (I) can be prepared in accordance with process step 2 as follows:

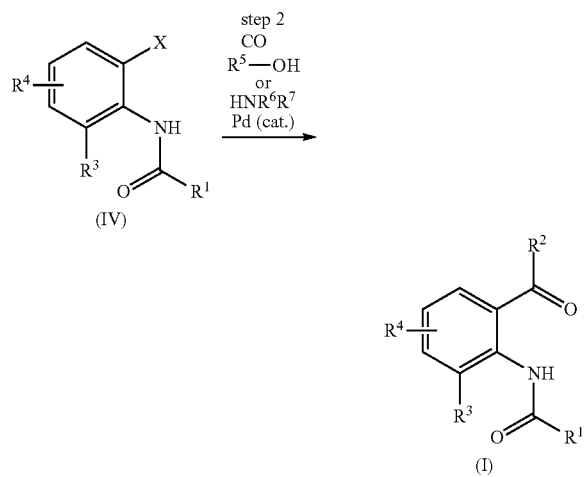

The reaction is performed in the presence of a palladium catalyst. The palladium catalysts used in the process according to the invention are palladium(II) salts, for instance palladium chloride, bromide, iodide, acetate or acetylacetonate, which may optionally be stabilized by further ligands, for example alkyl nitriles, or Pd(0) species, for example palladium on activated carbon, $Pd(PPh_3)_4$, bis(dibenzylideneacetone)palladium or tris(dibenzylideneacetone)dipalladium. Preference is given to bis(dibenzylideneacetone)palladium, tris(dibenzylideneacetone)dipalladium, palladium chloride, palladium bromide and palladium acetate; particular preference is given to bis(dibenzylideneacetone)palladium, palladium chloride and palladium acetate.

The amount of palladium catalyst used in the process according to the invention is 0.001 to 20 mole per cent, based on substituted anthranilic acid derivative of the general formula (IV) used. Preferably 0.005 to 10 mole per cent is used, more preferably 0.01 to 5 mole per cent.

The phosphine ligands used in the process according to the invention are ligands of the general formula (X)

$$PR^{10}R^{11}R^{12} \qquad (X)$$

where the $R^{10}$, $R^{11}$ and $R^{12}$ radicals are each independently hydrogen, linear or branched $C_1$-$C_8$-alkyl, vinyl, aryl or heteroaryl from the group of pyridine, pyrimidine, pyrrole, thiophene and furan, which may in turn be substituted by further substituents from the group of linear or branched $C_1$-$C_8$-alkyl or $C_6$-$C_{10}$-aryl, linear or branched $C_1$-$C_8$-alkyloxy or $C_1$-$C_{10}$-aryloxy, halogenated linear or branched $C_1$-$C_8$-alkyl or halogenated $C_6$-$C_{10}$-aryl, $C_6$-$C_{10}$-aryloxycarbonyl, linear or branched $C_1$-$C_8$-alkylamino, linear or branched $C_1$-$C_8$-dialkylamino, $C_1$-$C_8$-arylamino, $C_1$-$C_8$-diarylamino, hydroxyl, carboxyl, cyano and halogen such as fluorine or chlorine.

Further useful phosphine ligands include chelating bisphosphines. Examples of these include 1,2-bis(diphenylphosphino)ethane, 1,2-bis(diphenylphosphino)propane, 1,2-bis(diphenylphosphino)butane, 2,2'-bis (diphenylphosphino)-1,1'-binaphthyl and 1,1'-bis (diphenylphosphino)ferrocene.

Preferred phosphine ligands are trialkylphosphines such as tri-tert-butylphosphine and triadamantylphosphine, and also triarylphosphines such as triphenylphosphine, tri(ortho-tolyl)phosphine or tri(para-methoxyphenyl)phosphine. Particular preference is given to triphenylphosphine.

As an alternative to this, it is also possible to use defined palladium complexes which have been obtained from the abovementioned ligands in one or more process steps.

In the process according to the invention, 1-20 molar equivalents of phosphine are used, based on the amount of palladium used. Preferably 2-15 molar equivalents are used.

Process step 2 of the process according to the invention is performed in the presence of carbon monoxide (CO). The carbon monoxide is typically introduced in gaseous form, and so the reaction is usually performed in an autoclave. It is customary to work at CO pressure 0.1 to 50 bar, preferably at 1 to 25 bar.

It is alternatively also possible in principle to introduce the carbon monoxide in the form of suitable metal carbonyl complexes, for example dicobalt octacarbonyl or molybdenum hexacarbonyl. Preference is given to working with gaseous carbon monoxide.

Process step 2 is generally performed in the presence of a base. Suitable bases are organic bases such as trialkylamines, alkylpyridines, phosphazenes and 1,8-diazabicyclo [5.4.0]undecene (DBU). Preference is given to organic bases such as triethylamine, tripropylamine, tributylamine, diisopropylethylamine, pyridine, alkylpyridines, for example 2,6-dimethylpyridine, 2-methyl-5-ethylpyridine or 2,3-dimethylpyridine.

The compounds of the general formula (V) or (VI) required for preparation of the substituted anthranilic acid derivatives of the general formula (I) are typically used in an excess, based on the substituted anthranilic acid derivative of the general formula (IV). It is also possible to use the compounds of the general formula (V) or (VI) in such an amount that they simultaneously serve as solvents.

PREPARATION EXAMPLES

The Preparation Examples which follow illustrate the invention without limiting it.

Example 1

2-Acetamido-5-cyano-3-methylbenzoic acid

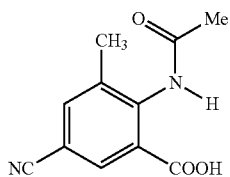 [SMILES: CC(=O)Nc1c(C)cc(C#N)cc1C(=O)O]

In a 30 ml autoclave, under nitrogen as protective gas, 2.54 g [10 mmol] of N-(2-bromo-4-cyan-6-methylphenyl) acetamide, 3.89 g [21 mmol] of tri-n-butylamine, 0.131 g [0.5 mmol] of triphenylphosphine, 0.035 g [0.05 mmol] of bis(triphenylphosphine)palladium(II) chloride and 2 g of water are combined. After closure, the autoclave is purged with carbon monoxide and heated to 110° C., and a carbon monoxide pressure of 10 bar is maintained. After 18 hours, the mixture is allowed to cool to room temperature, the autoclave is depressurized, the reaction mixture is stirred with methylene chloride and filtered through kieselguhr, and the filtrate is washed, first with dilute hydrochloric acid and then with water, dried over sodium sulphate and concentrated under reduced pressure. This gives 1.14 g of the title compound.

LC/MS: m/e=219 (MH$^+$).
GC/MS(sil.): m/e=362 (M$^+$, 2×sil., 10%), 347 (M$^+$–15, 2×sil., 45%).

Example 2

N-(2-Bromo-4-cyano-6-methylphenyl)-1-(3-chloropyridin-2-yl)-3-{[5-(trifluoromethyl)-2H-tetrazol-2-yl]methyl}-1H-pyrazole-5-carboxamide

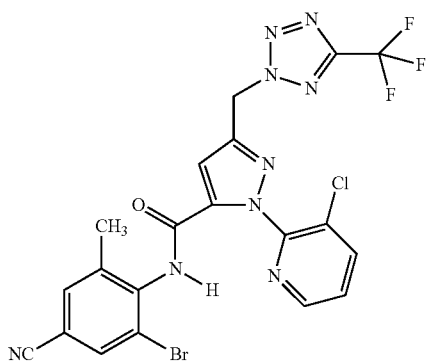 [SMILES: Cc1cc(C#N)cc(Br)c1NC(=O)c1cc(Cn2nnc(C(F)(F)F)n2)nn1-c1ncccc1Cl]

To a solution of 3.74 g of 1-(3-chloropyridin-2-yl)-3-{[5-(trifluoromethyl)-2H-tetrazol-2-yl]methyl}-1H-pyrazole-5-carboxylic acid in 20 ml of acetonitrile are added 1.86 g of 3-methylpyridine. Then 1.37 g of methanesulphonyl chloride are added dropwise at 0° C. After 30 minutes at 0° C., the red solution thus obtained is slowly added dropwise to a solution of 2.11 g of 4-amino-3-bromo-5-methylbenzonitrile and 1.12 g of 3-methylpyridine in 20 ml of acetonitrile. The reaction mixture is stirred at room temperature for one hour and at 40° C. for 1 hour and cooled to room temperature, water and methylene chloride are added thereto, and the organic phase is removed, washed with dilute hydrochloric acid, dried and concentrated. The crude product thus obtained is purified by chromatography on silica gel (cyclohexane/ethyl acetate). This gives 1.30 g of the title compound as a pale beige solid.

LC/MS: m/e=566 (MH$^+$ with $^{79}$Br and $^{35}$Cl).

Example 3

Methyl 2-({[1-(3-chloropyridin-2-yl)-3-{[5-(trifluoromethyl)-2H-tetrazol-2-yl]methyl}-1H-pyrazol-5-yl]carbonyl}amino)-5-cyano-3-methylbenzoate

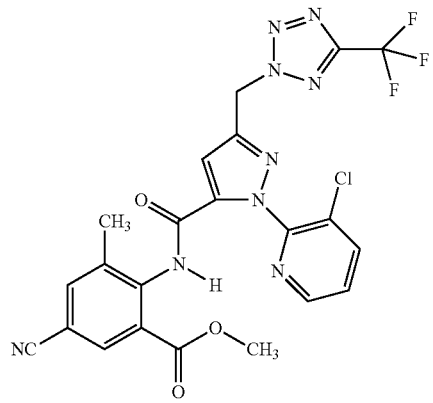 [SMILES: COC(=O)c1cc(C#N)cc(C)c1NC(=O)c1cc(Cn2nnc(C(F)(F)F)n2)nn1-c1ncccc1Cl]

In a 30 ml autoclave, under nitrogen as protective gas, 0.567 g of N-(2-bromo-4-cyano-6-methylphenyl)-1-(3-chloropyridin-2-yl)-3-{[5-(trifluoromethyl)-2H-tetrazol-2-yl]methyl}-1H-pyrazole-5-carboxamide, 0.463 g of tri-n-butylamine, 0.066 g of triphenylphosphine, 0.035 g of bis (triphenylphosphine)palladium(II) chloride and 10 ml of methanol are combined. After closure, the autoclave is purged with carbon monoxide and heated to 110° C., and a carbon monoxide pressure of 10 bar is maintained After 18 hours, the mixture is allowed to cool to room temperature, the autoclave is depressurized, the reaction mixture is stirred with methylene chloride and filtered through kieselguhr, and the filtrate is washed, first with dilute hydrochloric acid and then with water, dried over sodium sulphate and concentrated under reduced pressure. This gives 0.49 g of the title compound.

LC/MS: m/e=546 (MH$^+$ with $^{35}$Cl).

Example 4

1-(3-Chloropyridin-2-yl)-N-[4-cyano-2-(dimethyl-carbamoyl)-6-methylphenyl]-3-{[5-(trifluoromethyl)-2H-tetrazol-2-yl]methyl}-1H-pyrazole-5-carboxamide

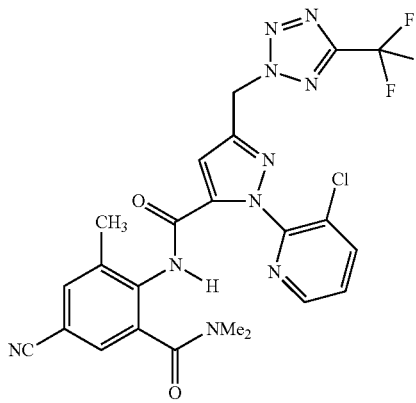

In a 30 ml autoclave, under nitrogen as protective gas, 0.567 g of N-(2-bromo-4-cyano-6-methylphenyl)-1-(3-chloropyridin-2-yl)-3-{[5-(trifluoromethyl)-2H-tetrazol-2-yl]methyl}-1H-pyrazole-5-carboxamide, 0.463 g of tri-n-butylamine, 0.066 g of triphenylphosphine, 0.035 g of bis(triphenylphosphine)palladium(II) chloride and 2 ml of dimethylamine are combined. After closure, the autoclave is purged with carbon monoxide and heated to 110° C., and a carbon monoxide pressure of 10 bar is maintained. After 18 hours, the mixture is allowed to cool to room temperature, the autoclave is depressurized, the reaction mixture is stirred with methylene chloride and filtered through kieselguhr, and the filtrate is washed, first with dilute hydrochloric acid and then with water, dried over sodium sulphate and concentrated under reduced pressure. This gives 0.475 g of the title compound.

LC/MS: m/e=559 (MH$^+$ with $^{35}$Cl).

The invention claimed is:
1. A compound of formula (IV)

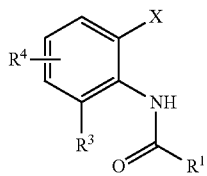

(IV)

where

R$^1$ is a hetaryl radical of the general formula (II)

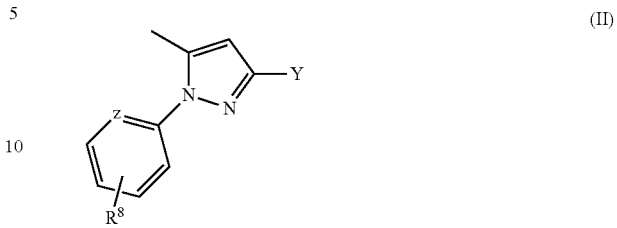

(II)

where

R$^8$ is fluorine or chlorine,

Z is N, and

Y is a radical of the general formula (III)

(III)

where

R$^9$ is CF$_3$ or C$_2$F$_5$,

R$^3$ is methyl,

R$^4$ is chlorine or cyano, and

X is bromine.

2. A compound of formula (IV) according to claim 1, wherein R$^8$ is fluorine.

3. A compound of formula (IV) according to claim 1, wherein R$^8$ is chlorine.

4. A compound of formula (IV) according to claim 1, wherein R$^9$ is CF$_3$.

5. A compound of formula (IV) according to claim 1, wherein R$^9$ is C$_2$F$_5$.

6. A compound of formula (IV) according to claim 1, wherein R$^4$ is chlorine.

7. A compound of formula (IV) according to claim 1, wherein R$^4$ is cyano.

* * * * *